United States Patent [19]
Horowitz et al.

[11] Patent Number: 5,905,052
[45] Date of Patent: May 18, 1999

[54] VANADYL PYROPHOSPHATE OXIDATION CATALYST PRECURSORS

[75] Inventors: Harold Saul Horowitz, Wilmington; Eugene Michael McCarron, III, Greenville, both of Del.

[73] Assignee: E. I. du Pont de Nemours and Company, Wilmington, Del.

[21] Appl. No.: 08/903,368

[22] Filed: Jul. 30, 1997

Related U.S. Application Data

[60] Provisional application No. 60/027,941, Oct. 8, 1996.
[51] Int. Cl.$^6$ .................................................. B01J 27/198
[52] U.S. Cl. ............................ 502/209; 502/208; 502/353
[58] Field of Search .................................. 502/208, 209, 502/353

[56] References Cited

U.S. PATENT DOCUMENTS

| | | |
|---|---|---|
| 3,864,280 | 2/1975 | Schneider . |
| 3,985,775 | 10/1976 | Harrison . |
| 4,043,943 | 8/1977 | Schneider ................................ 252/437 |
| 4,132,670 | 1/1979 | Katsumoto et al. .................... 252/437 |
| 4,442,226 | 4/1984 | Bither, Jr. .............................. 502/209 |
| 5,401,707 | 3/1995 | Benziger et al. ....................... 502/209 |
| 5,496,787 | 3/1996 | Hatano et al. .......................... 502/209 |
| 5,532,385 | 7/1996 | Benziger ................................ 502/209 |

OTHER PUBLICATIONS

G. Huan et al., Hydrothermal synthesis and characterization of vanadyl alkylphosphonates VORPO$_3$·H$_2$O, *Materials Chemistry and Physics*, 35, 199–204, 1993, No Month Available.

J. W. Johnson et al., Layered Compounds with Alternating Organic and Inorganic Layers: Vanadyl Organophosponates, *Inorg. Chem.*, 23, 3842–3844, 1984, No Month Available.

J. W. Johnson, Molecular Recognition of Alcohols by Layered Compounds with Alternating Organic and Inorganic Layers, *J. Am. Chem.*, 111, 381–383, 1989, No Month Available.

A. J. Jacobson et al., Chemical Modification of Vanadium Phosphates, *Mater. Sci. Mongraph.*, 28A, 469–472, 1985, No Month Available.

J. W. Johnson et al., Vanadyl Benzylphosphonates and Vanadyl Naphthylphosphonates: Intercalation Reactions with Butanols, *Chemistry of Materials*, 2, 198–201, 1990, No Month Available.

I. J. Ellison et al., Control of the Composition and Morphology of Vanadium Phosphate Catalyst Precursors from Alcohol Treatment of VOPO$_4$·2H$_2$O, *J. Chem. Soc., Chem. Commun.*, 1093–1094, No Month Available.

L. Alagna et al., A New Layered Vanadyl (IV) Phosphate With An Expanded Interlayer, *Mat. Res. Bull.*, 22, 691–699, 1987, No Month Available.

L. Benes et al., Intercalation of aliphatic amines into layered structure of vanadyl phosphate, *Inorganica Chimica Acta*, 177, 71–74, 1990, No Month Available.

L. Benes et al., Layer–type Complexes Consisting of VOSO$_4$ or VOPO$_4$ and Aliphatic Alcohols, *Inorganica Chimica Acta*, 114, 47–50, 1986, No Month Available.

V. V. Guliants et al., Synthesis and Characterization of Vanadyl Phosphite, V$^{IV}$OHP$^{III}$O$_3$·1.5H$_2$O, *Chem. Mater.*, 7, 1485–1492, 1995, No Month Available.

(List continued on next page.)

*Primary Examiner*—Elizabeth D. Wood

[57] ABSTRACT

Vanadyl pyrophosphate oxidation catalyst precursors comprise vanadium phosphate esters of the formula

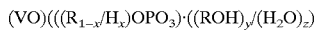

wherein, R is an alkyl group capable of bonding, through oxygen, to phosphorus to form a phosphate ester; x is 0 to about 0.5; y is 0–1.0; z is 0–1.25; and y+z is 0–1.25 are particularly useful for the selective oxidation of butane to maleic anhydride and readily thermally decompose to form the vanadyl pyrophosphate oxidation catalysts.

3 Claims, 1 Drawing Sheet

OTHER PUBLICATIONS

V. V. Guliants et al., Vanadyl(IV) Phosphonates, $VOC_nH_{2n+1}PO_{3x}H_2O$ (n=0–4, x=1 04 1.5) as Precursors of Vanadyl (IV) Pyrophosphate, $(VO)_2P_2O_7$, *Chem. Mater.*, 7,1493–1498, 1995, No Month Available.

V. V. Guliants et al., New Layered Vandyl(IV) Phosphite as a Precursor to Vanadyl Pyrophosphate Catalysts for Pattial Oxidation of n–Butane to Maleic Anhydride, *Journal of Catalysts*, 156, 298–300, 1995, No Month Available.

G. Huan et al., Hydrothermal Synthesis and Single–Crystal Structural Characterization of $(VO)_2[CH_2(PO_3)_2]$ $4H_2O$, *Journal of Solid State Chemistry*, 89, 220–225, 1990, No Month Available.

V. Soghomonian et al., Hydrothermal Synthesis and Structural Characterization of V(III)–Containing Phases of the Vanadium Organodiphosphonate System. Crystal Structures of the V(III) Species $(H_3O)[V_3(O_3PCH_2CH_2PO_3)(HO_3PCH_2CH_2PO_3H)_3]$ and of the Mixed Valence V(III)/V(IV) Material $(H_3O)_2[(VO)V_2(OH)_2(O_3PCH_2CH_2PO_3)_2]$ $H_2O$, *Chem. Mater.*, 7, 1648–1654, 1995, No Month Available.

C.C. Torardi et al., Transformation of $VOHPO_4$ $1/2H_2O$ to $(VO)_2P_2O_7$: Grystallographic, Microstructural, and Mechanistic Aspects, *Journal of Solid State Chemistry*, 119, 349–358, 1995, No Month Available.

L. Benes et al., Intercalation of Anhydrous Vanadyl Phosphate With Aliphatic Alcohol Mixtures, *Collect. Czech. Chem. Commun.*, 59, 1616–1619, 1994, No Month Available.

Sananes, Marie T. et al., n–Butane oxidation using catalysts prepared by treatment of $VOPO_42H_2O$ with octanol, *Journal of the Chemical Society, Faraday Transactions*, 92, No. 1, 137–142, Jan., 1996, No Month Available.

Kiely, Christopher, et al., Characterisation of Variations in Vanadium Phosphate Catalyst Microstructure with Preparation Route, *Journal of Catalysis*, 162, No. 1, 31–47, 1996, No Month Available.

Hutchings, Graham J. et al., Improved method of preparation of vanadium phosphate catalysts, *Catalysis Today*, 33, 161–171, 1997, No Month Available.

VANADYL PYROPHOSPHATE OXIDATION CATALYST PRECURSORS

This application claims the benefit of U.S. Provisional application No. 60/027,941, filed Oct. 8, 1996.

BACKGROUND OF THE INVENTION

This invention relates to vanadyl pyrophosphate oxidation catalyst precursors comprising vanadium phosphate esters and to a process of converting the precursors to vanadyl pyrophosphate oxidation catalysts by thermal decomposition.

Maleic anhydride is used as a raw material for numerous products, including agricultural chemicals, paints, paper sizing, food additives and synthetic resins. To fill the high demand for this valuable chemical, a variety of commercial processes have been developed for its production, the most successful of which involves the vapor phase oxidation of n-butane to maleic anhydride in the presence of a vanadyl pyrophosphate ("VPO") catalyst. Since the development of this method in the 1970's, research has continued to improve the reaction conditions and, particularly, the VPO catalysts.

A review of the improvements made in this technology is given by G. J. Hutchings, in *Applied Catalysis*, Elsevier Science Publishers B. V. Amsterdam, 72(1991), pages 1–31. The preferred method of preparation of VPO catalysts is the hydrochloric acid digestion of $V_2O_5$ and $H_3PO_4$ in either an aqueous solvent, as described, for example, in U.S. Pat. No. 3,985,775, or non aqueous solvent, such as methanol, tetrahydrofuran (THF) or isobutanol, followed by solvent removal to give what is termed the catalyst precursor, vanadium hydrogen phosphate, $VO(HOPO_3) \cdot (H_2O)0.5$. The precursor is then activated by heating, as described, for example, in U.S. Pat. No. 3,864,280 and U.S. Pat. No. 4,043,943. Other methods are described in U.S. Pat. No. 4,132,670 and U.S. Pat. No. 4,442,226.

Johnson et al. (*Inorg Chem.* 23, 3842 (1984); *J Am. Chem. Soc.* 111, 381 (1989)) have described a series of compounds given by the formula $VO(RPO_3) \cdot H_2O$ R'OH, where R' represent alkyl groups from alcohol molecules and R represent alkyl groups attached to phosphorus atoms. These compounds are described as vanadyl alkylphosphonates since the alkyl groups, R, are bound directly to the trivalent phosphorus. Alkyl groups expressed as $C_nH_{2n}+1$ for n=2–9, 14 and 18 are disclosed. While these compounds are layered, only those with n<3 and just $H_2O$ in the interlayer space have structures which are analogous to $VO(HOPO_3) \cdot (H_2O)0.5$. Thermogravimetric results of Huan et al. (*Materials Chemistry and Physics* 35, 199 (1993)) and Guliants et al. (*Chem. Mater.* 7, [8] 1493 (1995)) showed that complete thermal decomposition of these phases in air requires temperatures >500° C. and –375–475° C., respectively. Johnson et al. did not comment on the decomposition products. Guliants et al. did disclose that these compounds could be converted to VPO at temperatures lower than the vanadium hydrogen phosphate, $VO((HOPO_3) \cdot (H_2O)0.5$.

U.S. Pat. No. 5,401,707 describes a series of compounds with the general formula, $VO(HOPO_3) \cdot (H_2O)0.5$ $(\{C_nH_{2n}+\}- X)_z$ in which n has a value of from 0 to 20, z has a value of from about 1.5 to about 1.9; and X is an oxygen or nitrogen containing functional group. These phases consist of the known $VOHOP_3 \cdot (H_2O)0.5$ intercalated with a compound such as an alkyl amine. The conversion of these precursors to $(VO)_2P_2O_7$ at temperature of at least 400° C. is disclosed.

Alagna et al. (*Mat. Res. Bull.* 22, 691 (1987)) have described the synthesis of $VOHOPO_3 \cdot (H_2O)_{1.25} \cdot (EtOH)0.5$. This material is reported to have a basal plane spacing of 1.358 nm and a structure consisting of vanadyl hydrogen phosphate, $VO(OHPO_3) \cdot (H_2O)0.5$ whose layers are intercalated with ethanol molecules. The compound decomposes, non-topotactically, to an amorphous substance at ~400° C.

SUMMARY OF THE INVENTION

This invention provides VPO catalyst precursors of the general formula $$(VO)(((R)_{1-x}H_x)OPO_3) \cdot ((ROH)_y(H_2O)_z) \qquad [1]$$

wherein R=an alkyl group of the formula $C_nH_{2n+1}$, where n=1–12; x=0—0.5; y=0–1.0; z=0–1.25; and y+z=0–1.25.

In another aspect, the invention comprises a process of making vanadyl pyrophosphate oxidation catalysts comprising the step of thermally decomposing the precursors of formula [1].

DETAILED DESCRIPTION OF THE INVENTION

Figure 1:
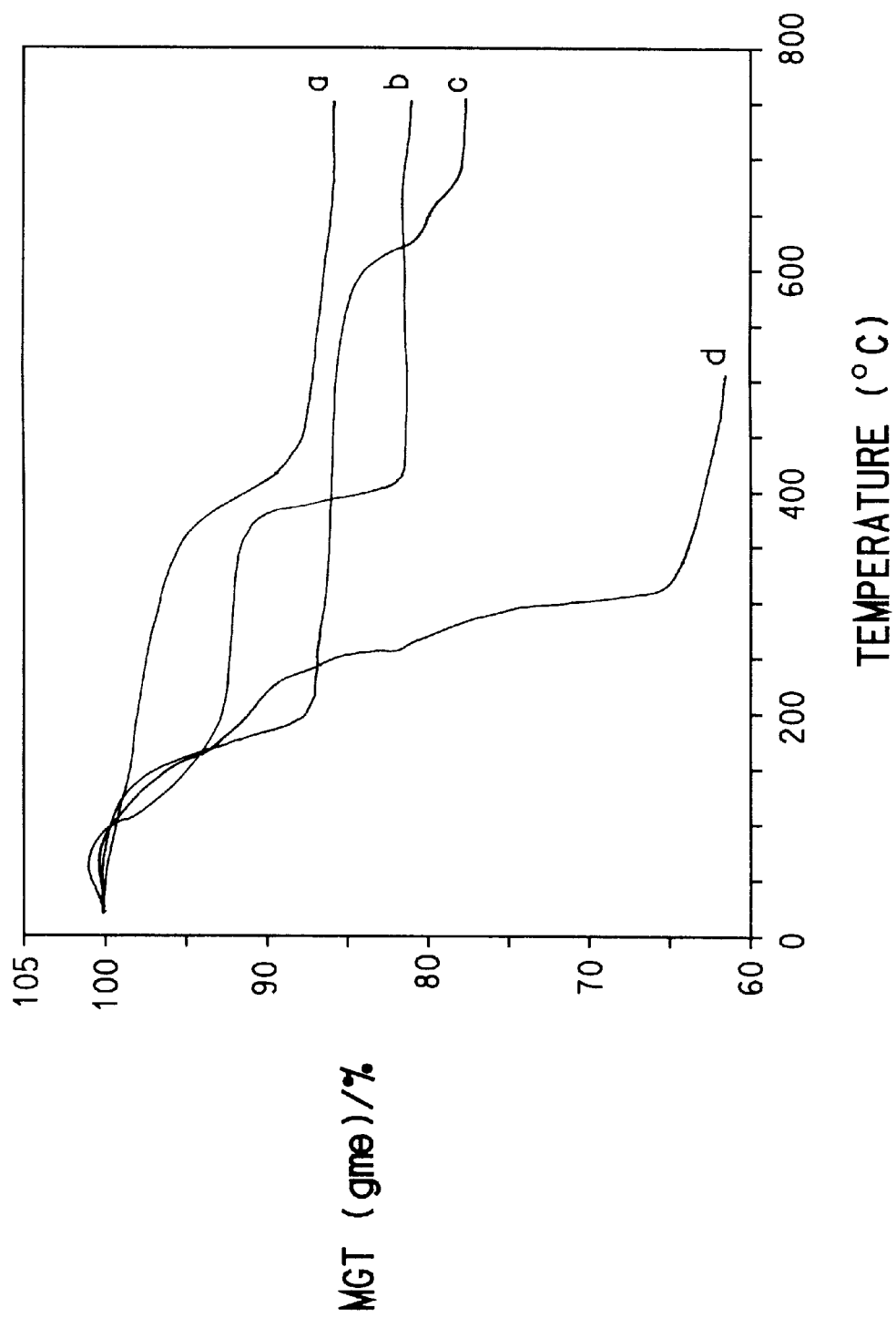
FIG. 1 is a graph of a thermogravimetric analysis of certain VPO precursors of this invention and VPO precursors of the prior art.

The catalyst precursors of this invention are analogous to the known $VO(HOPO_3) \cdot (H_2O)0.5$, but with alkyl groups and alcohol molecules substituted, to varying extents, for protons and water molecules, respectively.

In the precursors of this invention, the phosphorus is pentavalent as in the conventional vanadium hydrogen phosphate. The phosphate ester, which represents a structural element that is critical to the bonding scheme of these precursors has not been previously observed in vanadium phosphate or vanadium hydrogen phosphate based phases.

These precursors are preferably prepared by reacting a vanadium oxide, preferably $V_2O_5$, with a phosphorus oxide, preferably $P_2O_5$, in a predominantly alcoholic medium ROH, where R=an alkyl group of the formula $C_nH_{2n+1}$, where n=1–12 at ambient pressure and, preferably, at the reflux temperature of the particular alcohol. The formation of the vanadium organophosphate precursors requires the presence of primary alcohols and a relatively dry alcoholic medium. For example, the reaction of appropriate quantities of vanadium oxide (preferably $V_2O_5$) and phosphorus oxide (preferably $P_2O_5$) in a primary alcohol, ROH, where R represents an alkyl group $C_nH_{2n+1}$ (n=1 to 12), results in the compounds of formula [1] above. The reaction is carried out at ambient pressure and is typically conducted at the reflux temperature of the alcohol used. Lower temperatures can be used, but will result in a slower reaction rate.

The source of vanadium and phosphorus can alternatively be the compound $VOPO_4 \cdot 2H_2O$. Using $VOPO_4 \cdot 2H_2O$ rather than $V_2O_5$ plus $P_2O_5$ has the effect of increasing the values of x and z in formula [1]. In either case, additional $P_2O_5$, to provide a stoichiometric excess of phosphorus, can be used. The use of stoichiometric excesses of phosphorus by incorporation of the corresponding amount of $P_2O_5$ is found to decrease the value of x and increase the value of y in formula [1]. The use of stoichiometric excesses of $P_2O_5$ is also found to improve the reaction kinetics for the formation of the vanadium organophosphate phases of this invention.

While not wishing to be bound by this theory, we believe that the synthesis-related observations noted in the preceding paragraphs, can be rationalized by assuming the importance of phosphate esters as critical structural elements in these new compounds and, quite possibly, as reaction intermediates in their formation. The formation of phosphate esters relies upon a relatively low concentration of water, thereby precluding formation of the competing phosphate acid. Therefore, as one reduces the water content either by using $V_2O_5$ plus $P_2O_5$ instead of $VOPO_4 \cdot 2H_2O$, or by adding $P_2O_5$ in excess of the stoichiometric phosphorus requirements, the relative amounts of protons and water molecules, defined by x and z in formula [1], are decreased relative to alkyl groups and alcohol molecules. If an excessive amount of water is present in the reaction medium, the phosphate ester-based phase will not form at all. The preference for primary alcohols can be understood in terms of the recognized decrease in reactivity of esterification in the order primary>secondary>tertiary alcohols. This decrease in tendency is attributed to steric hindrance caused by the increasingly bulky groups as one encounters the higher order alcohols. Steric hindrance is also likely to explain why branched, primary alcohols exhibit poorer kinetics in forming phosphate ester-based precursors. Consequently, synthesis of the phosphate ester-based precursors derived from branched alcohols is more sensitive to the adverse effects of excessive water concentration than is the synthesis derived from linear alcohols.

As shown in the Table 1 below, the basal plane spacings increase with the length of the alkyl chain (n) and range from ~0.9 to 3.8 nm for n=1–12. The interplanar spacings shown in Table 1 are, in part, determined by the identity (and therefore the size) of the alkyl group and are not significantly affected by the extent of site occupation (i.e. the value of (1–x)) of these groups.

TABLE 1

| Sample | n | Solvent | Reaction Temp (°C.) | Layer spacing ($10^{-10}$ meters) |
|---|---|---|---|---|
|  | 0 | isobutanol | 105 | 5.69* |
| 6a | 1 | methanol | 65 | 9.05 |
| 6b | 2 | ethanol | 79 | 10.76 |
| 6c | 3 | 1-propanol | 95 | 11.93 |
| 6d | 4 | 1-butanol | 109 | 13.07 |
| 6e | 5 | 1-pentanol | 110 | 14.20 |
| 6f | 6 | 1-hexanol | 110 | 17.33 |
| 6g | 7 | 1-heptanol | 110 | 20.42 |
| 6h | 8 | 1-octanol | 110 | 25.68 |
| 6i | 9 | 1-nonanol | 110 | 28.00 |
| 6j | 12 | 1-dodecanol | 105 | 37.32 |

*This is the known $VO(HOPO_3) \cdot (H_2O)_{0.5}$ phase.

Thermal decomposition of these novel precursors to form the corresponding vanadyl pyrophosphate catalyst is found to generally occur at a lower temperature than either $VO(HOPO_3) \cdot (H_2O)0.5$ or any of the other prior art VPO precursors described above. For example, with reference to the results of thermogravimetric analysis experiments shown in FIG. 1, the phosphate butyl ester-based precursor of this invention decomposes at ~300° C. in $N_2$ (see FIG. 1, curve d), which is about 100° C. lower in temperature than the vanadyl hydrogen phosphate precursor under the same conditions (FIG. 1, curve a). The phosphonates did not decompose until >600° C. when similarly tested (FIG. 1, curve c). The phosphate methyl ester precursor of this invention, decomposing at ~400° C. in $N_2$, had the highest decomposition temperature of the phosphate esters. (FIG. 1, curve b) Accordingly, the precursors of this invention can be converted to the catalysts simpler and faster than prior art precursors.

Conducting the transformation in controlled oxygen partial pressure further lowers the decomposition temperatures and results in formation of the catalytically selective vanadyl pyrophosphate while avoiding the formation of less selective pentavalent vanadium phosphate phases. The use of lower temperatures also favors the synthesis of catalysts possessing higher surface area. The precursors of this invention have a plate-like morphology, essentially identical to the conventional vanadium hydrogen phosphate. Like the conventional precursor, these phosphate ester-based precursors appear to convert topotactically to the vanadyl pyrophosphate, thereby preserving this desirable morphology in the catalytically active phase into which they transform.

The Examples below serve to illustrate the practice of the invention.

EXAMPLE 1

Vanadium methyl phosphate ester was synthesized in the presence of a stoichiometric excess of phosphorus by charging a 500 ml round bottom flask equipped with a reflux condenser and a magnetic stirrer with 8.858 g (0.049 mole) $V_2O_5$, 8.35 g (0.059 mole) $P_2O_5$ and 200 cc methanol. The reactor was heated to 64±1° C. with the slurry continuously stirred and the reactor purged with nitrogen. The reaction was run for a total of 455 hr. with methanol added when required to compensate for losses due to volatility.

13.15 g of a blue green solid (not including several small samples extracted from the reactor earlier during the synthesis) was recovered by vacuum filtration. The recovered sample was then rinsed with 100 cc of methanol. The filtration and rinsing, as well as the subsequent drying at ambient temperature and pressure, were all conducted under nitrogen.

The powder X-ray diffraction pattern indicated a single phase vanadium phosphate ester with the following reflections:

| d-spacing ($10^{-10}$ meters) | relative intensity |
|---|---|
| 8.899 | 100 |
| 4.467 | 3 |
| 3.705 | 13 |
| 3.156 | 7 |
| 2.928 | 33 |
| 2.786 | 6 |
| 2.371 | 5 |
| 2.092 | 1 |
| 1.898 | 1 |
| 1.863 | 3 |

The first two peaks appear to be multiple order reflections and are consistent with the plate-like morphology observed for this powder. Assuming the first peak is the (001) reflection of a layered structure, the interplanar spacing of the basal planes is $8.899 \times 10^{-10}$ meters.

Decomposition of the compound in nitrogen occurs in two well defined steps at approximately 150° C. and 375° C., respectively.

As corroborated by the analyses shown below, the chemical formula of the powder product of this example is proposed to be $(VO)(CH_3OPO_3) \cdot CH_3OH$.

| elemental analysis | % observed | % calculated |
|---|---|---|
| V | 23.5 | 24.38 |
| P | 14.3 | 14.82 |

-continued

| elemental analysis | % observed | % calculated |
|---|---|---|
| C | 10.65 | 11.49 |
| H | 3.08 | 3.38 |
| H/C | 3.44 | 3.5 |

Thermogravimetric Analysis weight loss data

|  | Observed | Calculated |
|---|---|---|
| $CH_3OH$ (1st wt. loss step) | 15 | 15.33 |
| $(CH_3)_2O$, 1 mole evolved per mole precursor (2nd wt. loss step) | 10 | 11.02 |
| Total | 25 | 26.35 |

EXAMPLE 2

Another sample of vanadium methyl phosphate was prepared by adding 5 g $VOPO_4·2H_2O$ and 200 cc methanol to a 500 ml round bottom flask equipped with a reflux condenser and a magnetic stirrer. The reactor was heated to 62 ±1° C. with the slurry continuously stirred and the reactor purged with nitrogen. The reaction was run for a total of 455 hr. with methanol added when required to compensate for losses due to volatility. 4.36 g of a blue-green solid (not including several small samples extracted from the reactor earlier during the synthesis) was recovered by vacuum filtration. The recovered sample was then rinsed with 100 cc of methanol. The filtration and rinsing, as well as the subsequent drying at ambient temperature and pressure, were all conducted under nitrogen.

The powder X-ray diffraction pattern indicated a single phase vanadium phosphate ester with the following reflections:

| d-spacing ($10^{-10}$ meters) | relative intensity |
|---|---|
| 8.955 | 100 |
| 4.456 | 3 |
| 3.733 | 6 |
| 3.178 | 3 |
| 2.943 | 12 |
| 2.801 | 2 |
| 2.377 | 2 |
| 2.084 | 11 |
| 1.809 | 3 |

The first two peaks appear to be multiple order reflections and are consistent with the plate-like morphology observed for this powder. Assuming the first peak is the (001) reflection of a layered structure, the interplanar spacing of the basal planes is $8.955 \times 10^{-10}$ meters.

Decomposition of the compound in nitrogen, while heating at 10° C./min., occurs in two well defined steps at approximately 150° C. and 375° C., respectively.

As corroborated by the analyses shown below, the chemical formula of the powder product of this example is proposed to be

| elemental analysis | % observed | % calculated |
|---|---|---|
| V | 25.2 | 23.9 |
| P | 15.6 | 14.5 |
| C | 8.16 | 8.16 |
| H | 2.78 | 2.79 |
| H/C | 4.05 | 4.07 |

Thermogravimetric Analysis weight loss data

|  | Observed | Calculated |
|---|---|---|
| 0.3 $H_2O$/0.7 $CH_3OH$ (1st wt. loss step) | 13 | 13.05 |

EXAMPLE 3

Two samples of vanadium methyl phosphate ester were synthesized under identical reaction conditions, except that stoichiometric excesses of phosphorus in the amounts of 10 and 20 molar % were employed in reactions (a) and (b), respectively.

| reaction (a) | reaction (b) |
|---|---|
| 8.858 g (0.049 mole) $V_2O_5$ | 8.858 g (0.049 mole) $V_2O_5$ |
| 7.594 g (0.054 mole) $P_2O_5$ | 8.400 g (0.059 mole) $P_2O_5$ |
| 200 cc methanol | 200 cc methanol |

In each case, the reactants were added to a 500 ml round bottom flask equipped with a reflux condenser and a magnetic stirrer. The reactor was heated to 64±1° C. with the slurries continuously stirred and the reactors purged with nitrogen. The reactions were each run for a total of 334 hr. with methanol added when required to compensate for losses due to volatility.

Blue-green powder solids were recovered at various times during the course of these reactions. In the case of reaction (a) (10% molar excess of phosphorus), the reaction was still incomplete at 334 hr., as evidenced by the presence of a trace amount of unreacted $V_2O_5$ detected in the X-ray diffraction pattern. In the case of reaction (b) (20% molar excess of phosphorus), the solid was single phase vanadium methyl phosphate ester by 262 hr. After 334 hours of reaction, the remaining solids were recovered from each reactor by vacuum filtration. The recovered samples were then each rinsed with 200 cc of methanol and dried on the filter in ambient atmosphere and at ambient temperature for 18 hours.

The powder X-ray diffraction patterns indicate the formation of vanadium phosphate esters with basal plane (001) interplanar spacings of $9.090 \times 10^{-10}$ meters and $9.051 \times 10^{-10}$ meters, for reactions (a) and (b), respectively.

This example demonstrates that the use of phosphorus in amounts exceeding stoichiometry improve the kinetics of the synthesis reaction.

EXAMPLE 4

Vanadium propyl phosphate ester was synthesized by adding 8.858 g (0.049 mole) $V_2O_5$, 7.594 g (0.054 mole) $P_2O_5$ and 200 cc 1-propanol to a 500 ml round bottom flask equipped with a reflux condenser and a magnetic stirrer. The reactor was heated to 95±1° C. with the slurry continuously stirred and the reactor purged with nitrogen. The reaction was run for a total of 96 hours with propanol added when required to compensate for losses due to volatility.

After 96 hours of reflux, 12.21 g of a blue-gray solid (not including several small samples extracted from the reactor earlier during the synthesis) was recovered by vacuum filtration. The recovered sample was then rinsed with 100 cc of 1-propanol. The filtration and rinsing, as well as the subsequent 4 hours of drying at ambient temperature and pressure, were all conducted under nitrogen. The reaction appeared to have gone nearly to completion within 24 hours as evidenced by an X-ray pattern of vanadyl phosphate ester with only a slight trace of unreacted $V_2O_5$ observable. By 72 hours of reflux, the X-ray pattern appears to be single phase vanadyl phosphate ester with the following reflections:

| d-spacing ($10^{-10}$ meters) | relative intensity |
| --- | --- |
| 8.899 | 100 |
| 4.467 | 3 |
| 3.705 | 13 |
| 3.156 | 7 |
| 2.928 | 33 |
| 2.786 | 6 |
| 2.371 | 5 |
| 2.092 | 1 |
| 1.898 | 1 |
| 1.863 | 3 |

The first two peaks appear to be multiple order reflections and are consistent with the plate like morphology observed for this powder. Assuming the first peak is the (001) reflection of a layered structure, the interplanar spacing of the basal planes is $11.959 \times 10^{-10}$ meters.

This example, when compared vs. Example 3 (reaction a) above, demonstrates the improvement in reaction kinetics of the synthesis of the vanadyl phosphate esters by using a higher boiling solvent and thereby raising the reflux temperature at which the reaction is conducted.

EXAMPLE 5

A sample of vanadium methyl phosphate was prepared by adding 5 g $VOPO_4 \cdot 2H_2O$ and 200 cc methanol to a 500 ml round bottom flask equipped with a reflux condenser and a magnetic stirrer. The reactor was heated to 63±1° C. with the slurry continuously stirred and the reactor purged with nitrogen. The reaction was run for a total of 122.5 hr. with methanol added when required to compensate for losses due to volatility.

4.52 g of a blue-green solid was recovered by vacuum filtration. The recovered sample was then rinsed with 50 cc of methanol. The powder was subsequently dried in air at ambient temperature.

The powder X-ray diffraction pattern indicated a single phase vanadium phosphate ester with the following reflections:

| d-spacing ($10^{-10}$ meters) | relative intensity |
| --- | --- |
| 8.996 | 100 |
| 4.483 | 3 |
| 3.734 | 6 |
| 3.168 | 2 |
| 2.933 | 12 |
| 2.789 | 2 |
| 2.368 | 2 |

-continued

| d-spacing ($10^{-10}$ meters) | relative intensity |
| --- | --- |
| 2.085 | 7 |
| 1.813 | 1 |

The first two peaks appear to be multiple order reflections and are consistent with the plate-like morphology observed for this powder. Assuming the first peak is the (001) reflection of a layered structure, the interplanar spacing of the basal planes is $8.996 \times 10^{-10}$ meters.

This example, when compared vs. Example 3 (reaction a) and Example 3 (reaction b) above, demonstrate the superior reaction kinetics offered by $VOPO_4 \cdot 2H_2O$ as a reactant when synthesizing vanadyl phosphate esters based on primary linear alcohols. Presumably, this improvement in kinetics is a consequence of the atomic scale mixing of V and P that derives from using $VOPO_4 \cdot 2H_2O$ as a reactant. Even with no stoichiometric excess of phosphorus provided, the reaction proceeds to completion much more rapidly than similar syntheses, with excess phosphorus, using $V_2O_5$ and $P_2O_5$ as reactants. The basal plane (001) interplanar spacing is observed not to be heavily influenced either by the amount of excess phosphorus present in the reaction mixture or by the use of $VOPO_4 \cdot 2H_2O$ vs. $V_2O_5$ plus $P_2O_5$ as reactants.

EXAMPLE 6

Table 2 illustrates the broad range of vanadyl phosphate esters that can be prepared by the synthetic procedures described herein. The vanadyl phosphate esters listed in Table 2 have each been synthesized in the neat alcohol corresponding to the alkyl group, R, incorporated into the VPO precursor as indicated by the formula:

$$(VO)(((R)_{1-x}H_x)OPO_3) \cdot ((ROH)_y(H_2O)_z)$$

wherein x=0—0.5; y=0–1.0; z=0–1.25; and y+z=0–1.25. The first entry in Table 2, the previously well known and characterized $VO(HOPO_3) \cdot 0.5H_2O$, is included for comparative purposes.

TABLE 2

| Sample | n | Solvent | Reaction Temp (°C.) | Layer Spacing ($10^{-10}$ meters) |
| --- | --- | --- | --- | --- |
|  | 0 | isobutanol | 105 | 5.69* |
| 6a | 1 | methanol | 65 | 9.05 |
| 6b | 2 | ethanol | 79 | 10.76 |
| 6c | 3 | 1-propanol | 95 | 11.93 |
| 6d | 4 | 1-butanol | 109 | 13.07 |
| 6e | 5 | 1-pentanol | 110 | 14.20 |
| 6f | 6 | 1-hexanol | 110 | 17.33 |
| 6g | 7 | 1-heptanol | 110 | 20.42 |
| 6h | 8 | 1-octanol | 110 | 25.68 |
| 6i | 9 | 1-nonanol | 110 | 28.00 |
| 6j | 12 | 1-dodecanol | 105 | 37.32 |

*This is the known $VO(HOPO_3) \cdot (H_2O)_{0.5}$ phase.

EXAMPLE 7

Vanadium propyl phosphate ester was synthesized in the presence of a 20 molar % phosphorus by adding 8.858 g (0.049 mole) $V_2O_5$, 8.400 g (0.059 mole) $P_2O_5$ and 200 cc 1-propanol to a 500 ml round bottom flask equipped with a reflux condenser and a magnetic stirrer. The reactor was heated to 95±1° C. with the slurry continuously stirred and the reactor purged with nitrogen. The reaction was run for a total of 48 hr.

15.98 g of a blue gray solid was recovered by vacuum filtration. The recovered sample was then rinsed with 100 cc of 1-propanol. The sample was dried in air at ambient temperature for 5 hours.

The powder X-ray diffraction pattern indicated a vanadium phosphate ester with the following reflections:

| d-spacing ($10^{-10}$ meters) | relative intensity |
|---|---|
| 11.926 | 100 |
| 7.358 | 3 |
| 5.955 | 11 |
| 3.950 | 5 |
| 3.729 | 3 |
| 3.550 | 4 |
| 3.153 | 4 |
| 2.911 | 14 |
| 2.744 | 1 |
| 2.370 | 3 |
| 2.084 | 1 |
| 1.862 | 2 |

The first and third peaks appear to be multiple order reflections. Assuming the first peak is the (001) reflection of a layered structure, the interplanar spacing of the basal planes is $11.926 \times 10^{-10}$ meters.

A portion of the above sample was fired at 450° C. in flowing air for 1 hour. This sample was then evaluated for butane oxidation in a fixed bed reactor at 380° C. in 2% butane, 20% oxygen. A range of butane conversions was achieved by varying the contact time. The following data demonstrates the utility of a VPO catalyst derived from its corresponding vanadyl phosphate ester precursor for the selective oxidation of butane to maleic anhydride.

| Selectivity @ butane conversion of | | Yield to maleic anhydride @ contact time of | |
|---|---|---|---|
| 20% | 40% | 0.7 sec | 0.3 sec |
| 71% | 72% | 36.9% | 19.4% |

EXAMPLE 8

A vanadium phosphate ester was synthesized in the presence of a 20 molar % phosphorus by mixing 7.600 g (0.066 mole) 85% $H_3PO_4$ and 3.9560 g (0.026 mole) $P_2O_5$ to yield a 120% $H_3PO_4$ solution. This solution, together with 8.858 g (0.049 mole) $V_2O_5$ and 200 cc iso-butanol, were then added to a 500 ml round bottom flask equipped with a reflux condenser and a magnetic stirrer. The reactor was heated to 105±1° C. with the slurry continuously stirred and the reactor purged with nitrogen. The reaction was run for a total of 21 hr.

20.01 g of a blue solid (not including a small sample extracted from the reactor earlier during the synthesis) was recovered by vacuum filtration. The recovered sample was then rinsed with 200 cc of methanol. The sample was dried in air at ambient temperature for 5 hours.

The powder X-ray diffraction pattern indicated a vanadium phosphate ester with the following reflections:

| d-spacing ($10^{-10}$ meters) | relative intensity |
|---|---|
| 16.1198 | 10 |
| 8.0036 | 66 |
| 5.3598 | 31 |
| 3.5661 | 11 |
| 2.9430 | 48 |
| 2.3961 | 7 |
| 2.0863 | 11 |
| 1.8573 | 9 |

The first three peaks appear to be multiple order reflections. Assuming the first peak is the (001) reflection of a layered structure, the interplanar spacing of the basal planes is $16.120 \times 10^{-10}$ meters.

This example demonstrates that a vanadium phosphate ester phase can be derived from a non-linear primary alcohol. However, attempts at preparing this same phase by reaction of 100% $H_3PO_4$ in isobutanol with a reactant ratio of P/V=1.1) yielded only the vanadyl hydrogen phosphate, $VO(HOPO_3) \cdot 0.5H_2O$. Thus, the branched primary alcohols are kinetically less favorable for forming the phosphate ester phases than the linear primary alcohols. This kinetic limitation can be alleviated by lowering the water concentration of the reaction medium (i.e. increasing the concentration of the phosphoric acid).

EXAMPLE 9

A vanadium phosphate ester was synthesized in the presence of a stoichiometric excess of 20 molar % phosphorus by mixing 7.600 g (0.066 mole) 85% $H_3PO_4$ and 3.9560 g (0.026 mole) $P_2O_5$ to yield a 120% $H_3PO_4$ solution. This solution, along with 8.858 g (0.049 mole) $V_2O_5$ and 260 cc iso-pentyl alcohol was then added to a 500 ml round bottom flask equipped with a reflux condenser and a magnetic stirrer. The reactor was heated to 105±1° C. with the slurry continuously stirred and the reactor purged with nitrogen. The reaction was run for a total of 20.5 hr.

19.56 g of a blue solid was recovered by vacuum filtration. The recovered sample was then rinsed with 200 cc of acetone. The sample was dried under a nitrogen purge at ambient temperature for 6 hours.

The powder X-ray diffraction pattern indicated a vanadium phosphate ester with the following reflections:

| d-spacing ($10^{-10}$ meters) | relative intensity |
|---|---|
| 15.9598 | 43 |
| 7.9109 | 31 |
| 5.3254 | 14 |
| 4.7788 | 5 |
| 3.9796 | 7 |
| 3.5756 | 15 |
| 3.3689 | 19 |
| 3.1643 | 16 |
| 2.9307 | 100 |
| 2.3918 | 16 |
| 1.9521 | 6 |
| 1.8522 | 13 |
| 1.8388 | 8 |

The first, second, third, fifth and eighth peaks appear to be multiple order reflections. Assuming the first peak is the (001) reflection of a layered structure, the interplanar spacing of the basal planes is $15.960 \times 10^{-10}$ meters. This example demonstrates that a vanadium phosphate ester phase can be derived from a non-linear primary alcohol and requires a sufficiently dry reaction medium.

EXAMPLE 10

A vanadium phosphate ester was synthesized in a stoichiometric excess of 20 molar % phosphorus by combining 7.600 g (0.066 mole) 85% $H_3PO_4$ and 3.9560 g (0.026 mole) $P_2O_5$ to yield a 120% $H_3PO_4$ solution. This solution, along with 8.858 g (0.049 mole) $V_2O_5$ and 260 cc 2-methyl-1-butanol was then added to a 500 ml round bottom flask equipped with a reflux condenser and a magnetic stirrer. The reactor was heated to 104±1° C. with the slurry continuously stirred and the reactor purged with nitrogen. The reaction was run for a total of 20.5 hr.

19.82 g of a blue solid was recovered by vacuum filtration. The recovered sample was then rinsed with 200 cc of acetone. The sample was dried under a nitrogen purge at ambient temperature for 6 hours.

The powder X-ray diffraction pattern indicated a vanadium phosphate ester with the following reflections:

| d-spacing ($10^{-10}$ meters) | relative intensity |
|---|---|
| 16.3962 | 69 |
| 8.0472 | 35 |
| 5.8801 | 9 |
| 5.4027 | 18 |
| 2.9380 | 100 |
| 2.3875 | 11 |
| 1.9547 | 5 |
| 1.8564 | 14 |

The first second and fourth peaks appear to be multiple order reflections. Assuming the first peak is the (001) reflection of a layered structure, the interplanar spacing of the basal planes is $16.396 \times 10^{-10}$ meters.

This example demonstrates that a vanadium phosphate ester phase can be derived from a non-linear primary alcohol and requires a sufficiently dry reaction medium.

EXAMPLE 11

A vanadium phosphate ester was synthesized in a stoichiometric excess of 20 molar % phosphorus by melting neopentyl alcohol crystals to 70° C. to form a liquid, and then adding 260 cc of neopentyl alcohol, 8.858 g (0.049 mole) $V_2O_5$ and 8.350 g (0.059 mole) $P_2O_5$ to a 500 ml round bottom flask equipped with a reflux condenser and a magnetic stirrer. The reactor was heated to 105±1° C. with the slurry continuously stirred and the reactor purged with nitrogen. The reaction was run for a total of 22 hr.

12.37 g of a blue solid (not including a small sample extracted from the reactor earlier during the synthesis) was recovered by vacuum filtration. The recovered sample was then rinsed with 200 cc of acetone. The sample was dried under a nitrogen purge at ambient temperature for 6 hours.

The powder X-ray diffraction pattern indicated a vanadium phosphate ester with the following reflections:

| d-spacing ($10^{-10}$ meters) | relative intensity |
|---|---|
| 15.1532 | 100 |
| 7.5079 | 11 |
| 6.5859 | 4 |
| 5.8044 | 3 |
| 5.0628 | 4 |
| 2.9254 | 25 |
| 2.3414 | 3 |
| 2.0845 | 8 |

The first, second and fifth peaks appear to be multiple order reflections. Assuming the first peak is the (001) reflection of a layered structure, the interplanar spacing of the basal planes is $15.153 \times 10^{-10}$ meters.

This example demonstrates that a vanadium phosphate ester phase can be derived from a non-linear primary alcohol and, like examples 9 and 10, requires a sufficiently dry reaction medium. A previous attempt at preparing this phase by reacting $V_2O_5$ and 120% $H_3PO_4$ (by a procedure identical to examples 9 and 10) was not successful. This demonstrates that the more branched the alcohol, the poorer the kinetics for forming the phosphate ester and, consequently the need for an increasingly lower water concentration.

COMPARATIVE EXAMPLE 12

The synthesis of a vanadium phosphate ester was attempted using a 20 molar % phosphorus excess by adding 8.858 g (0.049 mole) $V_2O_5$, 7.600 g (0.066 mole) 85% $H_3PO_4$, 3.596 g (0.026 mole) $P_2O_5$ and 260 cc sec-butanol to a 500 ml round bottom flask equipped with a reflux condenser and a magnetic stirrer. The reactor was heated to 97±1° C. with the slurry continuously stirred and the reactor purged with nitrogen. The reaction was run for a total of 24 hr.

16.86 g of a blue solid (not including a small sample extracted from the reactor earlier during the synthesis) was recovered by vacuum filtration. The recovered sample was then rinsed with 100 cc of methanol. The sample was dried under a nitrogen purge at ambient temperature for 6 hours.

The powder X-ray diffraction pattern indicated the product was highly crystalline $VO(HOPO_3) \cdot 0.5H_2O$. A similar synthesis employing only $P_2O_5$ as the phosphorus source also yielded $VO(HOPO_3) \cdot 0.5H_2O$. This example demonstrates that higher order alcohols can not be used to form the vanadium phosphate esters, presumably because of the relative difficulty of forming phosphate esters that is encountered with secondary and tertiary alcohols (compared to primary alcohols).

EXAMPLE 13

Samples of vanadium methyl phosphate ester, vanadium butyl phosphate ester and vanadium isobutyl phosphate ester (prepared as described in examples 1, 6 and 8) were each fired at 10° C./min. to 750° C. in 0.5% and in 1.0% oxygen (balance nitrogen) and then immediately cooled to ambient temperature in nitrogen. X-ray diffraction showed that in each case only vanadyl pyrophosphate, $(VO)_2P_2O_7$, was present. Table 3 below indicates that each of the products exhibits an oxidation state close to 4.0, consistent with single phase vanadyl pyrophosphate.

TABLE 3

| | average vanadium oxidation state | |
|---|---|---|
| alcohol | 0.5% $O_2$ | 1.0% $O_2$ |
| methanol | 4.00 | 4.00 |
| butanol | 3.92 | 4.00 |
| iso-butanol | 4.02 | 4.05 |

This example demonstrates the utility of the vanadium phosphate esters as precursors to the catalytically useful (for selective partial oxidation of butane to maleic anhydride) phase, $(VO)_2P_2O_7$.

EXAMPLE 14

A vanadium phosphate ester was synthesized in the presence of a stoichiometric excess of 20 molar % phosphorus by adding 8.858 g (0.049 mole) $V_2O_5$ and 8.35 g (0.059 mole) $P_2O_5$ to 260 cc of 1-dodecanol in a 500 ml round bottom flask equipped with a reflux condenser and magnetic stirrer. The reactor was heated to 105° C. with the slurry continuously stirred and the reactor purged with nitrogen. The reaction was run for 24 hours.

35.20 grams of a blue-green solid was recovered by vacuum filtration. The recovered sample was then rinsed with 200 cc of acetone. The sample was dried under a nitrogen purge at ambient temperature for 18 hours.

The powder x-ray diffraction pattern indicated a vanadium phosphate ester with the following reflections:

| d-spacing ($10^{-10}$ meters) | relative intensity |
|---|---|
| 37.318 | 100 |
| 32.216 | 13 |
| 18.575 | 22 |
| 2.381 | 25 |
| 9.286 | 4 |
| 7.420 | 15 |
| 6.169 | 1 |
| 5.301 | 2 |
| 4.158 | 10 |
| 2.941 | 9 |

The first, third, fourth, sixth, seventh, eighth, and ninth peaks appear to be multiple order reflections. Assuming the first peak is the (001) reflection of a layered structure, the interplanar spacing of the basal planes is $37.318 \times 10^{-10}$ meters.

EXAMPLE 15

A vanadium phosphate ester was synthesized in the presence of a stoichiometric excess of 20 molar % phosphorus by adding 8.858 grams (0.049 mole) $V_2O_5$ and 8.35 g (0.059 mole) $P_2O_5$ to 110 cc phenyl ether ($C_{12}H_{10}O$) and 150 cc 1-dodecanol in a 500 ml round bottom flask equipped with a reflux condenser and magnetic stirrer. The reactor was heated to 103+/−2° C. with the slurry continuously stirred and the reactor purged with nitrogen. The reaction was run for 29 hours.

31.23 g of a green solid (not including a small sample extracted from the reactor earlier in the reaction) was recovered by vacuum filtration. The recovered solid was rinsed with 200 cc acetone and dried under a nitrogen purge at ambient temperature for 16 hours.

The powder x-ray diffraction pattern indicated a vanadium phosphate ester with the following reflections:

| d-spacing ($10^{-10}$ meters) | relative intensity |
|---|---|
| 36.135 | 100 |
| 18.192 | 28 |
| 12.147 | 31 |
| 9.116 | 5 |
| 7.342 | 7 |
| 6.082 | 2 |
| 5.208 | 3 |
| 4.377 | 10 |
| 4.184 | 12 |
| 2.941 | 10 |
| 2.878 | 4 |
| 2.083 | 5 |

The first, second, third, fourth, fifth, sixth, and seventh peaks appear to be multiple order reflections. Assuming the first peak is the (001) reflection of a layered structure, the interplanar spacing of the basal planes is $36.135 \times 10^{-10}$ meters.

A similar experiment using 260 cc of phenyl ether as a reaction solvent, and no 1-dodecanol, produced a solid which was predominantly $V_2O_5$ accompanied by $VOPO_4$ hydrate.

This experiment demonstrates that the synthesis of vanadium phosphate esters need not be carried out in neat alcohol reaction solvents. A relatively minor amount of the phosphate ester-forming alcohol in a non-aqueous inert solvent can be equally effective.

What is claimed is:

1. A vanadyl pyrophosphate oxidation catalyst precursor of the general formula $$(VO)(((R)_{1-x}H_x)OPO_3) \cdot ((ROH)_y(H_2O)_z).$$

wherein R=an alkyl group of the formula $C_nH_{2n}+1$, where n=1–12;

x=0—0.5;

y=0–1.0;

z=0–1.25; and y+z=0–1.25.

2. A process of making vanadyl pyrophosphate oxidation catalysts comprising the step of thermally decomposing a precursor of the general formula $$(VO)(((R)_{1-x}H_x)OPO_3) \cdot ((ROH)_y(H_2O)_z).$$

wherein R=an alkyl group of the formula $C_nH_{2n}+1$, where n=1–12;

x=0—0.5;

y=0–1.0;

z=0–1.25; and y+z=0–1.25 wherein the thermal decomposition step comprises heating the precursor at a temperature of 300° C.–600° C., said temperature being sufficient to decompose the precursor in an atmosphere that favors stabilization of tetravalent vanadium.

3. The process of claim 2 wherein the thermal decomposition step occurs at a temperature between 300° C.–400° C. in an inert atmosphere.

* * * * *